United States Patent [19]

Sawa

[11] 4,253,744
[45] Mar. 3, 1981

[54] OPTICAL SYSTEM FOR LIGHT MEASUREMENT OF AN EYE FUND

[75] Inventor: Seiji Sawa, Sakai, Japan

[73] Assignee: Minolta Camera Kabushiki Kaisha, Osaka, Japan

[21] Appl. No.: 36,311

[22] Filed: May 7, 1979

[30] Foreign Application Priority Data

May 12, 1978 [JP] Japan ................................. 53-56742

[51] Int. Cl.³ .............................................. A61B 3/10
[52] U.S. Cl. ...................................... 351/16; 128/666; 128/687; 128/745; 351/6
[58] Field of Search .................... 351/6, 7, 16; 354/62; 128/666, 645, 745, 687

[56] References Cited

U.S. PATENT DOCUMENTS

| | | | |
|---|---|---|---|
| 3,893,447 | 7/1975 | Hochheimer et al. | 351/9 X |
| 4,157,708 | 6/1979 | Imura | 128/666 |

OTHER PUBLICATIONS

Laing et al., "The Choroidal Eye Oximeter: An Instrument for Measuring Oxygen Saturation of Choroidal Blood In Vivo", *IEEE Transactions on Biomedical Engineering*, vol. BME-22, No. 3, pp. 183-195.

*Primary Examiner*—Paul A. Sacher
*Attorney, Agent, or Firm*—Jackson, Jones & Price

[57] ABSTRACT

In a light measuring optical system for use in measurement of pulse waves in the artery at the eye fundus or oxygen saturation in the artery blood at the eye fundus, light for illuminating the eye fundus is converged on the surface of the cornea of the eye to be measured and enters the interior of the eye through a small area within the pupil. Light reflected at the surface of the cornea is converged and blocked at its converging position while the light reflected from the eye fundus is allowed to pass by the light blocking member and reach a photocell. Coupled with the photocell is an electric circuit which transmits AC component of photocell output when DC component of the same assumes its minimum value.

9 Claims, 5 Drawing Figures

OPTICAL SYSTEM FOR LIGHT MEASUREMENT OF AN EYE FUND

BACKGROUND OF THE INVENTION

1. Field of the Invention

The present invention relates to an optical system for use in light measurement of an eye fundus, especially of the human, for detecting pulse waves in the artery at the eye fundus or detecting oxygen saturation in the artery blood at the eye fundus.

2. Description of the Prior Art

In devices for the observation of the eye fundus, eye fundus cameras have been known. The eye fundus cameras are designed to take pictures of the eye fundus with a flash illumination which continues for a very short time so that they are not affected by the movement of the eye to be photographed. However, when it is desired to measure or detect optically pulse waves in the artery at the eye fundus or oxygen saturation in the artery blood at the eye fundus, the optical system for the eye fundus camera can not be used without experiencing noise problems caused by movement of the eye during a time period required for the measurement or detection.

The prior art optical system for an eye fundus camera is arranged such that the light for illuminating the eye fundus is introduced to the eye through a centerapertured reflector which is disposed in front of the eye with its reflecting surface being inclined with respect to the optical axis of the camera and the light entering the eye and reflected at the eye fundus is directed to a camera through the center aperture of the reflector. With this optical system, the ray, which has a ring shape in cross section when passing through the pupil of the eye because of the center apertured configuration of the reflector, is partially blocked or obscured by the iris defining the pupil, as shown in the lower view of FIG. 1 when the eye moves a little from the position as shown in the upper view of FIG. 1, even if the ring R of the cross section of entering light has a smaller diameter than the pupil. Accordingly, the amount of light entering the eye for the illumination of the eye fundus varies with the movement of eye. In case of eye fundus camera employing such an optical system, such variation in the amount a minor illumination light may be of problem, because picture taking is carried out within a very short time. However, in the case of measurement of a pulse wave or the oxygen saturation in the blood vessel at the eye fundus, a considerable time period is required for the measurement of the light reflected from the eye fund so that the variation of the eye-fundus-illuminating light due to the movement of eye during that time can not be ignored. Such variation of illuminating light will reduce the S/N ratio in the resulting light measurement.

SUMMARY OF THE INVENTION

Accordingly, a primary object of the present invention is to provide an optical system suitable for light measurement of an eye fundus for a period of time.

Another object of the present invention is to provide an optical system suitable for measurement or detection of pulse waves or oxygen saturation in the blood vessel at the eye fundus.

Still another object of the present invention is to provide a light measuring system for measuring an eye fundus without being affected by the movement of an eye to be measured.

Further object of the present invention is to provide a light measuring system which photoelectrically measures an eye fundus with minimum affection of noise factors.

Still further object of the present invention is to provide a light measuring system for the photoelectric measurement of an eye fund wherein a reliable result may be obtained.

Yet another object of the present invention is to provide an electric circuit for transmitting to a indicator and/or recorder an output signal from a photocell which receives the light from the eye fundus, when the DC component of the output, i.e. the component varying at a low frequency, shows the least change.

Yet a further object of the present invention is to provide an electric circuit which can derive signals including minimum fluctuations, from the output of a photocell receiving a light reflected from the eye fundus.

Still yet a further object of the present invention is to provide a light measuring system for an eye fundus which provides a measured value at a condition when the eye is normally focused.

According to the present invention, light rays for illumination are converged on the cornea of an eye to be measured, so that the illumination light rays enter the eye through a narrow area which will be within the light transmisive area of the pupil of the eye even if the eye moves, e.g. because of fatigue during the measurement time period. Thus, the amount of illumination light entering the eye is kept constant, without the light entering area at the eye surface being eclipsed by the iris. In addition, any part of illumination light blocked from entering the eye and reflected by the iris will not impinge on a light detecting photoelectric element as a noise. Further, as the illumination light ray is concentrated on the surface of the cornea, the light rays reflected by the cornea can be converged at a point different from a point where the light rays reflected at the eye fundus is converged through the crystal lens of the eye. Thus, the light reflected by the cornea can easily be blocked at its converging point, with the light reflected at the eye fundus being allowed to reach the photoelectric element for the eye fundus measurement. Consequently, the optical system according to the present invention enables a highly reliable and accurate measurement of the eye fundus.

The above and other objects and features of the invention will appear more fully hereinafter from a consideration of the following description taken in connection with the accompanying drawings.

DETAILED DESCRIPTION OF THE INVENTION

Figure 1:
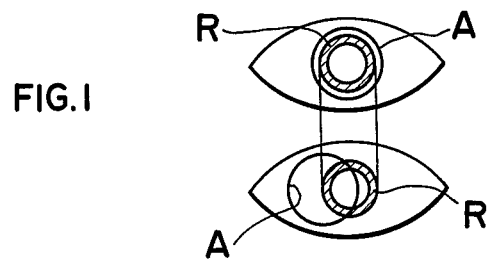
FIG. 1 is a schematic illustration of a front view of an eye for the explanation of the prior art.
Figure 2:
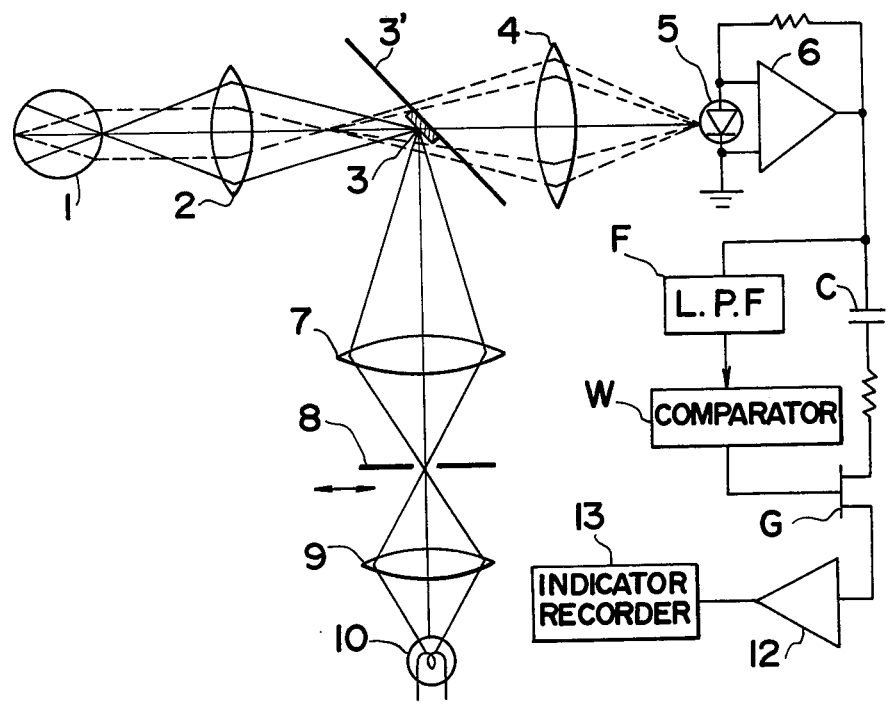
FIG. 2 is a schematic and diagramatic illustration of an optical system and a circuit according to an embodiment of the present invention.

With reference to FIG. 2, a small mirror 3 is disposed in front of a human eye 1 with its reflecting surface being inclined at 45° with the optical axis extending through the eye 1. The small mirror 3 may be a small area consisting of a layer of light reflecting material, such as aluminum, on a transparent glass plate 3'. A converging lens 2 is disposed between the eye 1 and the small mirror 3 to converge the light reflected from the small mirror 3 on the surface of the cornea of the eye 1. The light from a lamp 10 as an illumination light source is converged through a convex lens 9 on a pin hole plate 8, and the light passing through the pin hole of the plate 8 is again converged by a convex lens 7 on the small mirror 3 to form an image of the pin hole thereon. The pin hole plate 8 is shiftable laterally in the direction shown by an arrow for the adjustment of the pin hole position. It is to be noted that the pin hole plate may be removed if the light source has a small light emitting portion which can be regarded as a point source as in the case of an LED. The light incident on the small mirror 3 is reflected thereby and converged once again by the lens 2 on the surface of the cornea of the eye 1 to enter the interior of the eye 1 through its pupil and illuminates the eye fundus, i.e. the base or bottom of the eye.

The light reflected at the eye fundus is emitted from the eye 1 parallelly due to the lens function of the crystal lens of the eye 1, and passes through the non-coated transparent portion of the glass plate 3' after being converged at the focal point of the lens 2. The light passed through the glass plate 3' is then converged by a convex lens 4 on a photocell 5 such as a photodiode. As the small mirror 3 and the surface of the cornea are in an optically conjugate relationship with respect to the lens 2, the light ray reflected from the eye fundus and emitted or emerged outward parallelly through the cornea is converged before reaching the glass plate 3', the off-center portion of the light ray diverging from the focal point of the lens 2 can pass through the glass plate at the transparent portion arround the small mirror 3, although the central portion of the diverging light ray is blocked by the mirror 3.

Figure 3:
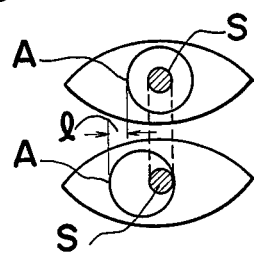
FIG. 3 is a schematic illustration of a front view of an eye for the explanation of the function of the optical system shown in FIG. 2.

With the optical arrangement as depicted above, the area S (see FIG. 3) through which the illumination light enters the interior of the eye 3 is or can be made considerably small in comparison with the area A of the eye pupil, so that the light passing area S will be within the pupil A even if the human eye moves to shift the pupil from the position aligned with the optical axis of the light measuring optical system extending through the lens 2, the mirror 3 and the lens 4, or even if the pupil is small depending on the human individual to be examined or on the ambient light condition. Accordingly, the light illuminating the eye fundus is kept constant during the measurement. The permissible amount l of the shifting of the pupil is estimated to be approximately 2 mm according to an experiment by the inventor. Further, the above depicted optical arrangement according to the present invention has another advantage in that light incident on the eye surface does not impinge on the iris which otherwise may reflect the incident light and directed it to the photocell 5 to cause noises in the light measurement thereby.

Figure 4:
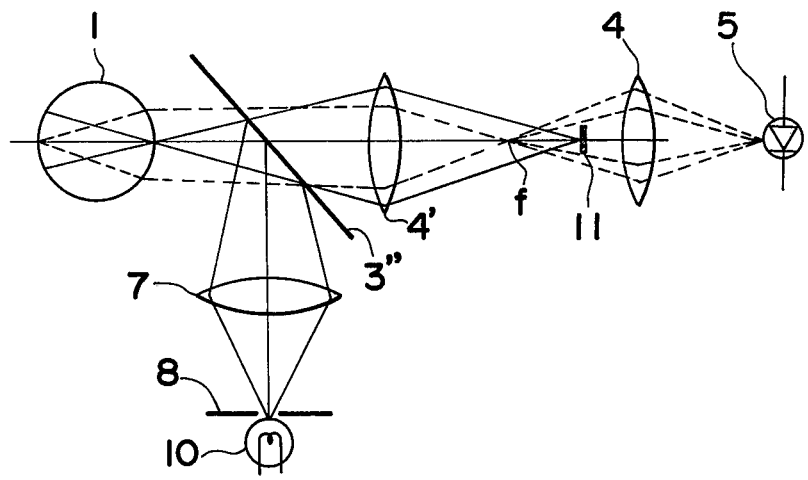
FIG. 4 is a schematic illustration of an optical system according to another embodiment of the present invention.

With reference to FIG. 4 showing another embodiment of the present invention, using the same reference numerals as those of FIG. 2 for corresponding elements, the illumination light emitted from the lamp 10 and passing through the pin hole of the plate 8 is directly converged on the eye surface, i.e. the surface of the cornea of the eye 1, by the convex lens 7 via a semitransparent mirror 3''. The light reflected at the eye fundus and emerged outward parallelly through the eye lens and crystal lens, passes through the semitransparent mirror 3'' and is converged by a lens 4' at its focal point f. The light diverging from the focal point f is then converged by the convex lens 4 on the photocell. On the other hand, a portion of the light converged on the eye surface is reflected therefrom as a diverging light ray and passes through the semi-transparent mirror 3''. However, the eye surface reflection light ray is converged by the lens 4' at the rear of the focal point f, i.e. at a position more distant from the lens 4' than the focal point f. Therefore, the eye surface reflection light can be blocked by an opaque plate 11 disposed at that converging portion, with the light reflected from the eye fundus being permitted to reach the photocell through the portion outside of the opaque plate 11 and through the convex lens 4. In contrast to this, the small mirror 3 of the FIG. 2 arrangement serves to block the eye surface reflection light as well as to direct the light from the lamp 10 to the eye 1.

Referring back to FIG. 2, the circuit processing the output of the photocell 5 is designed such that the output of the photocell 5 which has been reliable, steady and of high accuracy due to the optical system according to the present invention, is transmitted in a further stabilized condition to a signal processing and indicator and/or recorder stage of the circuit. This electric stabilizing process is preferrable because the light ray parallelly emerged from the eye become somewhat divergent or convergent due to fluctuation of focusing condition of the eye. When such divergence and convergence occur, the light incident on the photocell 5 is a little out-of-focused or defocused to vary the output of the photocell at a frequency lower than that of the pulse wave in the blood vessel at the eye fundus due to the variation of the blood current running therethrough. The circuit shown in FIG. 2 is designed to derive an AC component of the output of the photocell 5, i.e. a signal of the pulse wave, at the moment when the variation due to the fluctuation of eye focusing is minimum.

Figure 5:
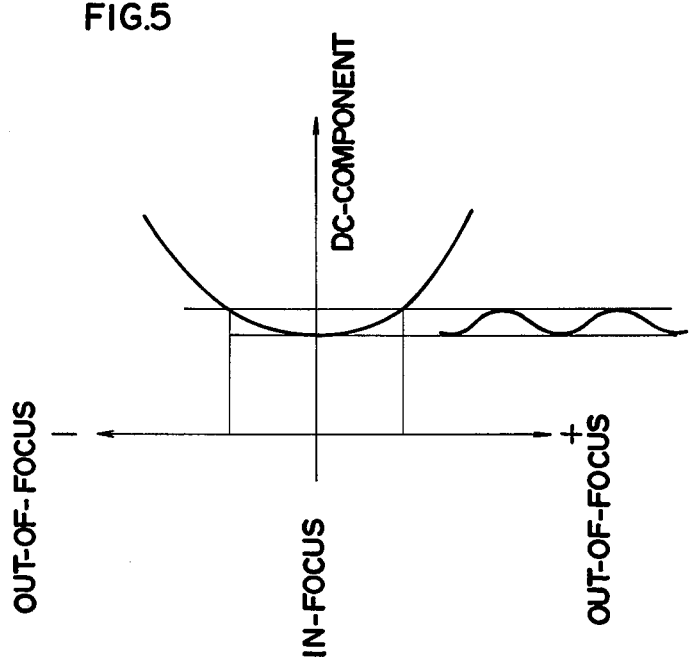
FIG. 5 is a diagram for the explanation of the operation of the circuit shown in FIG. 2.

In the Figure, the output of the photocell 5, after being amplified by an amplifier 6, is supplied to a capacitor C where the DC component of the output is cut off and the remaining AC component is transmitted through a gate member G (shown in the form of a FET in the Figure) to an amplifier 12 which in turn has its output connected with an indication and/or recorder 13 for the indication and/or recording of the output of the photocell. It will be apparent to those of ordinary skill in the art that the indicator and/or recorder device 13 may include, depending on the desired indication or record, a signal processing circuit having for example anologue to digital converter, digital calculator, and a circuit for providing signals suitable for controlling an indicator and/or recorder. The amplified output of the photocell 5 is also supplied to a low pass filter F which cuts off the high frequency component and allows passage of a low frequency component of having frequency lower than that of the pulse wave so that the output of the low pass filter F shows a gentle variation. The output of the low pass filter F is applied to a window-type level detector or comparator W which opens the gate and allows the passage of the pulse wave signals from the capacitor C to the amplifier 12 when its input from the low pass filter F has a value between predetermined levels. The lower of such levels may have a value Vo which is a little lower than a minimum level expected for the signal from the low pass filter F, and the other may be of the value obtained by adding a small amount of voltage $\Delta V$ to the lower level Vo, i.e. the other level will be Vo+$\Delta V$. With this arrangement, the indicator and/or recorder 13 is supplied with a signal of pulse wave at the condition when the DC component of the photocell output assumes the minimum value. As the DC component, i.e. the component varying at a frequency lower than that of the pulse wave, shows least change or variation when it assumes its minimum or approximately minimum value, the stability and reliability of the measured value are further advanced. FIG. 5 shows a relationship between the focusing condition of the eye and the DC component of the photocell output. As the value of DC component increases when the focusing of the eye deviates from a normal condition in any direction, the above depicted circuit system wherein the output is transmitted to the indicator and/or recorder when the DC component of photocell output assumes the minimum value, can provide an indication and/or recorded signal at the condition when the eye is normally focused.

While preferred embodiments of the invention have been described using specific terms, such description is for illustrative purpose only, and it is to be understood that charges and variations may be made without departing from the spirit or scope of the following claims.

I claim:

1. An eye fund measuring system for illuminating the fundus of an eye to be measured and measuring the light reflected from the fundus, comprising:
   a light source having a small light emitting area;
   a first converging means for converging the light from the light source on a surface of the eye;
   a second converging means for converging the light reflected at the surface of the eye;
   a photoelectric element for detecting the light from the eye fundus;
   a light blocking means for blocking the light reflected at the surface of the eye at the position where the surface reflected light is converged by said second converging means, said light blocking means allowing the light from the eye fundus to pass by to said photoelectric element; and
   a responsive means responsive to the output of said photoelectric element to provide a measurement of the light contacting the photoelectric element.

2. An eye fundus measuring system as claimed in claim 1 wherein said light source includes a lamp and a restricting member for restricting the cross sectional area of the light ray emitted from the lamp and passing through the restricting member.

3. An eye fundus measuring system as claimed in claim 1 further comprising a reflector disposed between the eye and said photoelectric element for directing the light from said light source to the eye, said reflector being so constructed as to allow passage of the light from the eye fundus to said photoelectric element.

4. An eye fundus measuring system as claimed in claim 4 wherein said reflector includes a semi-transparent mirror.

5. An eye fundus measuring system as claimed in claim 4 wherein said reflector includes a total reflection mirror, and said second converging means includes a first converging lens for converging the light reflected at the eye surface on said total reflection mirror, and a second converging lens for converging the light reflected by said total reflection mirror on the eye surface, said second converging lens also functioning as said second converging means, with said total reflection mirror functioning as said light blocking means.

6. An eye fundus measuring system as claimed in claim 1 wherein said responsive means includes an electric high pass filter for passing a high frequency component of the output of said photoelectric element, an electric low pass filter for pass a low frequency component of the output and gate means for transmitting said high frequency component therethrough when the low frequency component assumes its minimum value.

7. An eye fundus measuring system as claimed in claim 6 wherein said responsive means includes an indicator responsive to the high frequency component transmitted by said gate means.

8. An improved eye fund optical measuring system for providing a continuous measurement of the condition of blood in the eye fundus by measuring the light reflected from the eye fundus, comprising;
   a light source at a finite distance from a position at which an eye of a patient is to be measured;
   first means for converging the light from the light source at a focal point substantially coincident with the exterior surface of the cornea of the eye, and having a cross-sectional area considerably smaller than the pupil area of the patient's eye;
   second means for converging both the light reflected from the cornea and the light reflected from the eye fundus at separate focal points;
   means for eliminating the further progressive transmission of the cornea reflected light, located at substantially the focal point of the reflected cornea light, while permitting the transmission of the reflected light from the eye fundus, and
   means for measuring the reflected eye fundus light.

9. The invention of claim 8 wherein the means for measuring the reflected eye fundus light includes filter means for providing a high frequency signal and a low frequency signal from the measured light and gate means responsive to a predetermined value of the low frequency signal to provide a measurement of the condition of the patient's blood with the high frequency signal.

* * * * *

UNITED STATES PATENT AND TRADEMARK OFFICE
CERTIFICATE OF CORRECTION

PATENT NO. : 4,253,744
DATED : March 3, 1981
INVENTOR(S) : Seiji Sawa

It is certified that error appears in the above—identified patent and that said Letters Patent is hereby corrected as shown below:

Column 2, line 9, delete "fund" and insert --fundus--.

Claim 1, line 34, delete "fund" and insert --fundus--.

Claim 8, line 31, delete "fund" and insert --fundus--.

Signed and Sealed this

Fourteenth Day of July 1981

[SEAL]

Attest:

GERALD J. MOSSINGHOFF

Attesting Officer    Commissioner of Patents and Trademarks